(12) United States Patent
Kasuya et al.

(10) Patent No.: US 11,633,716 B2
(45) Date of Patent: *Apr. 25, 2023

(54) IMMUNOSUPPRESSIVE PROTEIN ADSORPTION MATERIAL AND ADSORPTION COLUMN

(71) Applicants: TORAY INDUSTRIES, INC., Tokyo (JP); NATIONAL UNIVERSITY CORPORATION SHIGA UNIVERSITY OF MEDICAL SCIENCE, Otsu (JP)

(72) Inventors: Junichi Kasuya, Otsu (JP); Ryo Matsunaga, Otsu (JP); Yoshiyuki Ueno, Otsu (JP); Yuji Ueda, Osaka (JP); Kazuo Teramoto, Otsu (JP); Kazumasa Ogasawara, Otsu (JP)

(73) Assignees: TORAY INDUSTRIES, INC., Tokyo (JP); NATIONAL UNIVERSITY CORPORATION SHIGA UNIVERSITY OF MEDICAL SCIENCE, Otsu (JP)

(*) Notice: Subject to any disclaimer, the term of this patent is extended or adjusted under 35 U.S.C. 154(b) by 503 days.

This patent is subject to a terminal disclaimer.

(21) Appl. No.: 16/638,586

(22) PCT Filed: Sep. 7, 2018

(86) PCT No.: PCT/JP2018/033126
§ 371 (c)(1),
(2) Date: Feb. 12, 2020

(87) PCT Pub. No.: WO2019/049961
PCT Pub. Date: Mar. 14, 2019

(65) Prior Publication Data
US 2020/0246776 A1 Aug. 6, 2020

(30) Foreign Application Priority Data
Sep. 8, 2017 (JP) .............................. JP2017-173238

(51) Int. Cl.
*B01J 20/26* (2006.01)
*A61M 1/36* (2006.01)
(Continued)

(52) U.S. Cl.
CPC ............ *B01J 20/26* (2013.01); *A61M 1/3687* (2013.01); *B01J 20/28011* (2013.01);
(Continued)

(58) Field of Classification Search
CPC ............ B01J 20/28011; B01J 20/28016; B01J 20/28; B01J 20/28023; B01J 20/28038;
(Continued)

(56) References Cited

U.S. PATENT DOCUMENTS

| 5,136,032 A * | 8/1992 | Nagamatsu ............ B01D 39/14 536/123 |
| 2001/0021525 A1 | 9/2001 | Hirai et al. |
| 2014/0017667 A1 | 1/2014 | Ogasawara et al. |

FOREIGN PATENT DOCUMENTS

| CN | 1053046 A | 7/1991 |
| EP | 0 431 593 A2 | 6/1991 |

(Continued)

OTHER PUBLICATIONS

International Search Report, issued in PCT/JP2018/033126, PCT/ISA/210, dated Dec. 11, 2018.
(Continued)

*Primary Examiner* — Clare M Perrin
(74) *Attorney, Agent, or Firm* — Birch, Stewart, Kolasch & Birch, LLP

(57) ABSTRACT

An objective of the present disclosure is to provide an adsorption material that has a carrier material with retained physical strength, and efficiently adsorbs an immunosuppressive protein. The present disclosure provides an adsorption material for immunosuppressive protein. The adsorp-
(Continued)

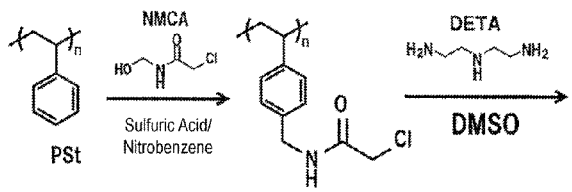

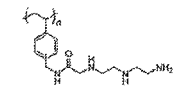

Structure Where One Terminal Primary Amino Group Reacts

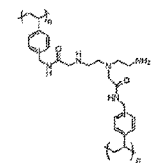

Structure Where One Terminal Primary Amino Group and Secondary Amino Group React (Cross-Linkage)

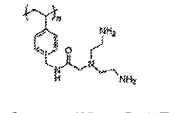

Structure Where Secondary Amino Group Reacts

Structure Where Both Terminal Primary Amino Groups React (Cross-Linkage)

Structure Where All Amino Groups React (Cross-Linkage)

tion material includes a water-insoluble carrier to which at least one nitrogen-containing compound selected from a polyamine represented by a predetermined formula and aliphatic amines represented by predetermined formulae is bound. A total content of amino groups on the water-insoluble carrier is more than 0 μmol and 2500 μmol or less per 1 g, and a content of primary amino groups on the water-insoluble carrier is 450 μmol or less per 1 g.

14 Claims, 2 Drawing Sheets

(51) Int. Cl.
*B01J 20/28* (2006.01)
*B01J 20/32* (2006.01)
*C07K 14/495* (2006.01)

(52) U.S. Cl.
CPC ....... *B01J 20/3219* (2013.01); *B01J 20/3248* (2013.01); *C07K 14/495* (2013.01); *B01J 20/28004* (2013.01); *B01J 20/28016* (2013.01)

(58) Field of Classification Search
CPC ... B01J 20/321; B01J 20/3219; B01J 20/3248
See application file for complete search history.

(56) References Cited

FOREIGN PATENT DOCUMENTS

| EP | 1532993 A1 | 5/2005 |
|---|---|---|
| JP | 2003-339854 A | 12/2003 |
| JP | 2006-272075 A | 10/2006 |
| JP | 2007-202634 A | 8/2007 |
| JP | 2011-139806 A | 7/2011 |
| JP | 2012-5827 A | 1/2012 |
| JP | 2012-62259 A | 3/2012 |
| WO | WO 03/101511 A1 | 12/2003 |
| WO | WO 2012/133399 A1 | 10/2012 |

OTHER PUBLICATIONS

Written Opinion of the International Searching Authority, issued in PCT/JP2018/033126, PCT/ISA/237, dated Dec. 11, 2018.
Extended European Search Report dated Apr. 26, 2021, in European Patent Application No. 18853817.7.
Chinese Office Action and Search Report for Chinese Application No. 201880054437.X, dated Jan. 28, 2022.

* cited by examiner

IMMUNOSUPPRESSIVE PROTEIN ADSORPTION MATERIAL AND ADSORPTION COLUMN

TECHNICAL FIELD

The present disclosure relates to an adsorption material for immunosuppressive protein, and an adsorption column including the same.

BACKGROUND ART

It has been becoming clear that cancers closely relate to immunity. Recently, it has been reported that concentrations of immunosuppressive blood components rise in many advanced cancers.

A representative immunosuppressive blood component is a Transforming Growth Factor-β (TGF-β). Recently, it has been becoming clear that an enhancement of an immunosuppressive signal involving the TGF-β, which is one of the molecules involved in a development of cancer, protects cancer cells from an attack by an immune system, and, as a result, the cancer progresses. The TGF-β is a protein that has a molecular weight of approximately 25,000 alone, and five isoforms (TGF-β1, TGF-β2, TGF-β3, TGF-β4, and TGF-β5) exist. In blood, the TGF-β exists in a state of binding to a protein referred to as a Latency Associated Peptide (hereinafter, referred to as a LAP) having a molecular weight of approximately 75,000 (hereinafter, referred to as a LAP-bound TGF-β).

While as a method for treating cancer, there has been developed medicines that block the immunosuppressive signal involving the TGF-β emitted from cancer cells, it has not yet reached an effective treatment.

Meanwhile, removing the TGF-β deactivates the signal for protecting the cancer cells from the immune system, and enhances immune strength of a patient. Therefore, regression of tumor and suppression of cancer progression can be expected.

As a material that adsorbs a protein, there has been disclosed several materials in which a compound is immobilized to a water-insoluble carrier. For example, Patent Literature 1 discloses a material in which lysine is immobilized to a water-insoluble carrier as a material that adsorbs a protein or a peptide having a kringle sequence. Patent Literature 2 discloses an adsorption carrier to which a functional group having an amino group is introduced. The adsorption carrier adsorbs inflammatory cytokines, such as a high-mobility group protein. Patent Literature 3 discloses an adsorbent that contains a polyamine derivative represented by a predetermined formula as an active ingredient for removing denatured low-density lipoprotein and/or advanced glycation end products. Patent Literature 4 discloses an adsorption material made of a base material having a polyamine as a material that adsorbs cytokines and/or superantigens.

Furthermore, Patent Literatures 5 and 6 disclose an adsorbing material in which a hydrophilic amino group (quaternary ammonium group) is immobilized to a water-insoluble carrier as a material that adsorbs the LAP-bound TGF-β3.

Patent Literature 7 discloses an adsorption device for adsorbing or removing leukocytes and cytokines with a predetermined pore diameter and a predetermined pore volume ratio to which a hydrophilic amine residue is bound.

CITATION LIST

Patent Literature

Patent Literature 1: JP 2012-062259 A
Patent Literature 2: JP 2012-005827 A
Patent Literature 3: JP 2011-139806 A
Patent Literature 4: JP 2006-272075 A
Patent Literature 5: WO 2003/101511
Patent Literature 6: JP 2003-339854 A
Patent Literature 7: JP 2007-202634 A

SUMMARY OF INVENTION

Technical Problem

However, Patent Literatures 1 to 4 do not disclose a technique for enhancing adsorbability of the immunosuppressive protein, such as the TGF-β. The quaternary ammonium group and the hydrophilic amine residue immobilized to the materials disclosed in Patent Literatures 5 to 7 have high hydrophilicity, and therefore, it is conceivable that there are cases where enhancing adsorption efficiency is difficult while maintaining physical strength of the carrier material.

Therefore, it is desired to develop an adsorption material that ensures efficiently adsorbing the TGF-β or the LAP-bound TGF-β in blood while maintaining the physical strength of the carrier material.

Therefore, an objective of the present disclosure is to provide an adsorption material that retains physical strength of a carrier material and efficiently adsorbs an immunosuppressive protein.

Solution to Problem

The inventors found that a polyamine residue or an aliphatic amine residue contained in a water-insoluble carrier adsorbs an immunosuppressive protein. Furthermore, it was found that when a total content of amino groups on the water-insoluble carrier and a content of primary amino groups on the water-insoluble carrier are within predetermined ranges in addition to containing the polyamine residue or the aliphatic amine residue in the water-insoluble carrier, the physical strength of a carrier material is retained and the immunosuppressive protein (in particular, the TGF-β or the LAP-bound TGF-β) can be efficiently adsorbed, and thus, the present disclosure has been completed.

Exemplary aspects of the embodiment are described below.

[1] An adsorption material for immunosuppressive protein, the adsorption material including
a water-insoluble carrier to which at least one nitrogen-containing compound is bound, the nitrogen-containing compound being selected from a polyamine represented by following Formula (1), a primary aliphatic amine represented by following Formula (2), and a secondary aliphatic amine represented by Formula (3),
wherein a total content of amino groups on the water-insoluble carrier is more than 0 µmol and 2500 µmol or less per 1 g, and a content of primary amino groups on the water-insoluble carrier is 450 µmol or less per 1 g.

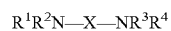  Formula (1)

[In Formula (1), X is a saturated or unsaturated aliphatic hydrocarbon group having 2 to 20 carbon atoms, or a heteroatom-containing carbon chain in which 1 to 5 carbon atoms of a saturated or unsaturated aliphatic hydrocarbon group having 3 to 20 carbon atoms are replaced with a nitrogen atom, a hydrogen atom that bonds to the nitrogen atom may be replaced with an alkyl group that may have an amino group, and $R^1$ to $R^4$ are each independently a hydrogen atom or an alkyl group.]

Formula (2)

[In Formula (2), $R^5$ is a saturated or unsaturated aliphatic hydrocarbon group having 1 to 12 carbon atoms.]

Formula (3)

[In Formula (3), $R^6$ and $R^7$ are each independently a saturated or unsaturated aliphatic hydrocarbon group having 1 to 12 carbon atoms.]

[2] The adsorption material according to [1],
wherein the nitrogen-containing compound comprises the polyamine represented by the Formula (1).

[3] The adsorption material according to [1] or [2],
wherein the nitrogen-containing compound binds to the water-insoluble carrier via a linker.

[4] The adsorption material according to any one of [1] to [3],
wherein the total content of amino groups is 30 to 2400 μmol per 1 g.

[5] The adsorption material according to [4],
wherein a proportion of the content of primary amino groups to the total content of amino groups (the content of primary amino groups/the total content of amino groups) is 0.30 or less.

[6] The adsorption material according to any one of [1] to [5],
wherein the water-insoluble carrier has a form of fiber or particle,
wherein the fiber or the particle has a diameter of 15 to 50 μm, and
wherein the water-insoluble carrier has a surface with an arithmetic mean roughness of 0.1 to 3.0 μm.

[7] The adsorption material according to any one of [1] to [6],
wherein the immunosuppressive protein is a TGF-β or a LAP-bound TGF-β.

[8] An adsorption column including the adsorption material according to any one of [1] to [7].

[9] The adsorption column according to [8],
wherein the adsorption column is used for a blood purification therapy.

ADVANTAGEOUS EFFECTS OF INVENTION

The present disclosure ensures providing an adsorption material that retains physical strength of a carrier material and efficiently adsorbs an immunosuppressive protein (in particular, a TGF-β or a LAP-bound TGF-β).

DESCRIPTION OF EMBODIMENTS

Figure 1:
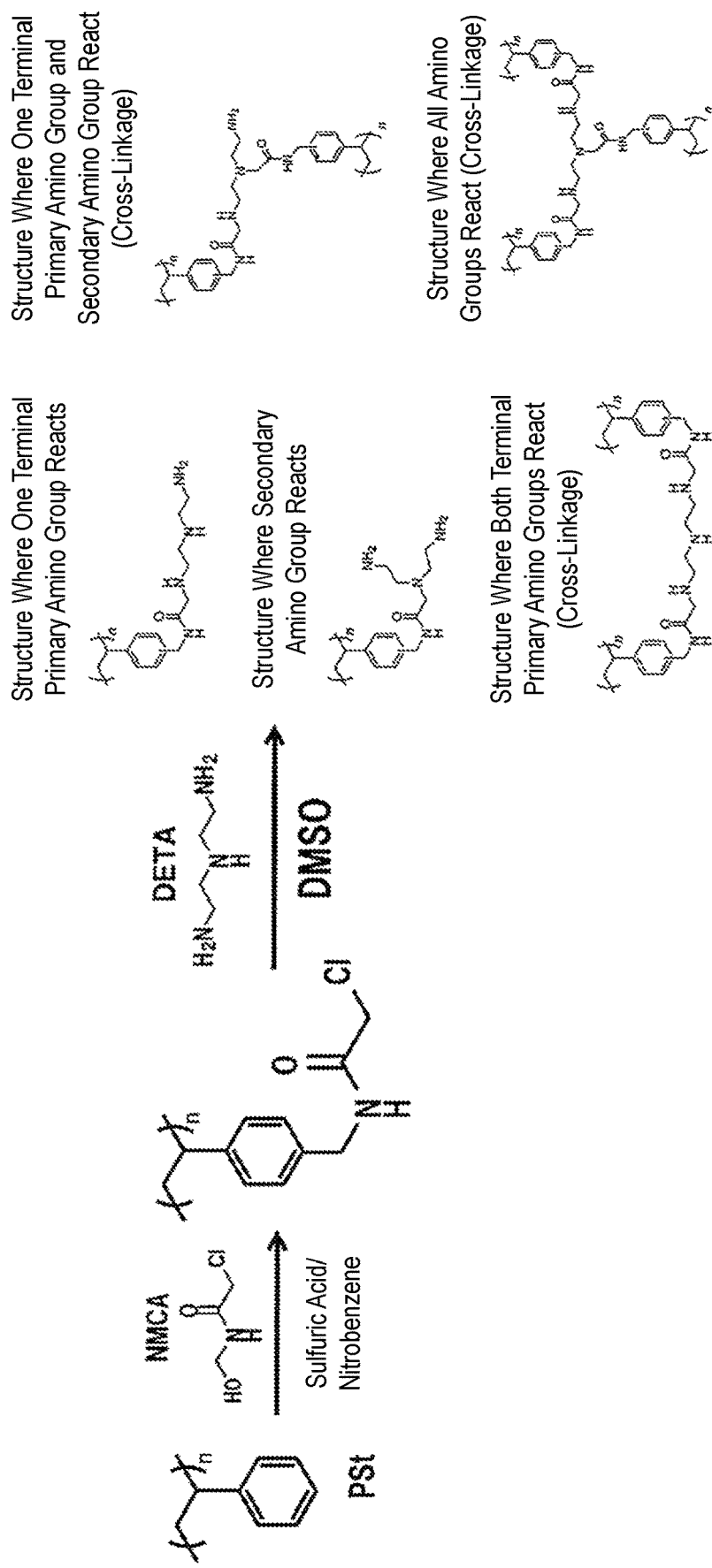
FIG. 1 is a conceptual diagram illustrating exemplary structures obtained when diethylenetriamine is immobilized on a water-insoluble carrier.

The following describes an embodiment further in details. It should be understood that throughout the entire Description, the expression as a singular form also includes a concept of its plural form unless otherwise stated. Accordingly, articles of a singular form (for example, in the case of English, "a," "an," and "the") should be understood as including the concept of its plural form unless otherwise stated. Terms used in the Description should be understood as used with meanings usually used in the technical field unless otherwise stated. Accordingly, unless otherwise defined differently, all the technical terms and the science and technology terms used in the Description have the same meanings as terms generally understood by a person skilled in the art pertaining to the present disclosure. In the case of inconsistency, the Description (including definition) has priority.

An adsorption material according to the embodiment relates to an immunosuppressive protein adsorption material for adsorbing an immunosuppressive protein. The adsorption material according to the embodiment includes a water-insoluble carrier to which at least one nitrogen-containing compound selected from a polyamine represented by Formula (1), a primary aliphatic amine represented by Formula (2), and a secondary aliphatic amine represented by Formula (3) is bound. In the adsorption material according to the embodiment, a total content of amino groups on the water-insoluble carrier is more than 0 μmol and 2500 μmol or less per 1 g of adsorption material and a content of primary amino groups on the water-insoluble carrier is 450 μmol or less per 1 g of adsorption material.

The "amino groups on the water-insoluble carrier" means a primary amino group (—$NH_2$), a secondary amino group, a tertiary amino group, and a quaternary amino group (quaternary ammonium group) that exist on the water-insoluble carrier. When the nitrogen-containing compound binds to the water-insoluble carrier, the primary amino group, the secondary amino group, the tertiary amino group, and/or the quaternary amino group exist in the nitrogen-containing compound after binding depending on a binding position in the nitrogen-containing compound. For example, when the polyamine represented by Formula (1) binds to the water-insoluble carrier, the primary amino group, the secondary amino group, the tertiary amino group, and/or the quaternary amino group exist in the polyamine after binding depending on the binding position in the polyamine. The nitrogen-containing compound preferably binds to the water-insoluble carrier via an amino group (or a nitrogen atom) in the compound. In the Description, the "amino groups on the water-insoluble carrier" is a concept that at least includes the primary amino group, the secondary amino group, the tertiary amino group, and the quaternary amino group derived from the nitrogen-containing compound thus generated. When the nitrogen-containing compound binds via a linker, the "amino group on the water-insoluble carrier" includes the primary amino group, the secondary amino group, the tertiary amino group, and the quaternary amino group derived from the linker.

The "total content of amino groups" means a total content (μmol) of primary amino groups, secondary amino groups, tertiary amino groups, and quaternary amino groups on the water-insoluble carrier. A "primary amino group on the water-insoluble carrier" means the primary amino group existing on the water-insoluble carrier. The "primary amino group on the water-insoluble carrier" is a concept that at least includes the primary amino group remained in the nitrogen-containing compound (for example, the polyamine) without reaction.

When it is used in the Description, a "nitrogen-containing compound residue" means a group obtained by directly or indirectly binding the nitrogen-containing compound to the water-insoluble carrier. Similarly, a "polyamine residue" means a group obtained by directly or indirectly binding the polyamine represented by Formula (1) to the water-insoluble carrier, and an "aliphatic amine residue" means a group obtained by directly or indirectly binding the aliphatic amine represented by Formula (2) or Formula (3) (also referred to as the aliphatic amine) to the water-insoluble carrier.

The nitrogen-containing compound is selected from the polyamine represented by Formula (1), the primary aliphatic amine represented by Formula (2), and the secondary aliphatic amine represented by Formula (3). For the nitrogen-containing compound, one kind may be used alone or a plurality of kinds may be used in combination.

In one embodiment, the nitrogen-containing compound is the polyamine represented by Formula (1).

$R^1R^2N-X-NR^3R^4$   Formula (1)

[In Formula (1), X is a saturated or unsaturated aliphatic hydrocarbon group having 2 to 20 carbon atoms, or a heteroatom-containing carbon chain in which 1 to 5 carbon atoms of a saturated or unsaturated aliphatic hydrocarbon group having 3 to 20 carbon atoms are replaced with a nitrogen atom, a hydrogen atom that bonds to the nitrogen atom may be replaced with an alkyl group that may have an amino group, and $R^1$ to $R^4$ are each independently a hydrogen atom or an alkyl group.]

In Formula (1), X is, for example, a saturated or unsaturated aliphatic hydrocarbon group having 2 to 20 (for example, 16 or less, 14 or less, 12 or less, 10 or less, 8 or less, 6 or less, and 4 or less) carbon atoms. In Formula (1), X is, for example, a heteroatom-containing carbon chain in which 1 to 5 (for example, 1 to 3) carbon atoms of a saturated or unsaturated aliphatic hydrocarbon group having 3 to 20 (for example, 16 or less, 14 or less, 12 or less, and 10 or less) carbon atoms are replaced with a nitrogen atom. The hydrogen atom that bonds to the nitrogen atom may be replaced with an alkyl group (for example, having 1 to 6 (preferably, 1 to 4) carbon atoms) that may have an amino group. $R^1$ to $R^4$ are each independently a hydrogen atom or an alkyl group. The alkyl group, for example, has 1 to 6 (preferably, 1 to 4) carbon atoms. The aliphatic hydrocarbon group may be linear or may be branched chain.

The polyamine represented by Formula (1) is preferred to be a polyamine represented by any one of the following Formulae (1-1) to (1-6).

$H_2N-(CH_2)_{p1}-NH_2$   Formula (1-1)

[In Formula (1-1), p1 is an integer from 2 to 12 (preferably, 2 to 6, 2 to 5, or 2 to 4), and at least one of the hydrogen atoms of the primary amino groups at both ends may be replaced with an alkyl group.], $H_2N-(CH_2)_{p1}-NH-(CH_2)_{p2}-NH_2$   Formula (1-2)

[In Formula (1-2), p1 and p2 are each independently an integer from 2 to 5 (preferably, 2 to 4, 2 or 3, or 2), the hydrogen atom of the secondary amino group may be replaced with an alkyl group that may have an amino group, and at least one of the hydrogen atoms of the primary amino groups at both ends may be replaced with an alkyl group.],

$H_2N-(CH_2)_{p1}-NH-(CH_2)_{p2}-NH-(CH_2)_{p3}-NH_2$   Formula (1-3)

[In Formula (1-3), p1, p2, and p3 are each independently an integer from 2 to 5 (preferably, 2 to 4, 2 or 3, or 2), the hydrogen atoms of the secondary amino groups may be each independently replaced with an alkyl group that may have an amino group, and at least one of the hydrogen atoms of the primary amino groups at both ends may be replaced with an alkyl group.],

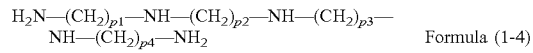

$H_2N-(CH_2)_{p1}-NH-(CH_2)_{p2}-NH-(CH_2)_{p3}-NH-(CH_2)_{p4}-NH_2$   Formula (1-4)

[In Formula (1-4), p1, p2, p3, and p4 are each independently an integer from 2 to 5 (preferably, 2 to 4, 2 to 3, or 2), the sum of p1, p2, p3, and p4 is 17 or less, the hydrogen atoms of the secondary amino groups may be each independently replaced with an alkyl group that may have an amino group, and at least one of the hydrogen atoms of the primary amino groups at both ends may be replaced with an alkyl group.],

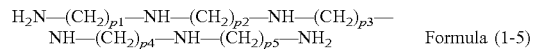

$H_2N-(CH_2)_{p1}-NH-(CH_2)_{p2}-NH-(CH_2)_{p3}-NH-(CH_2)_{p4}-NH-(CH_2)_{p5}-NH_2$   Formula (1-5)

[In Formula (1-5), p1, p2, p3, p4, and p5 are each independently an integer from 2 to 5 (preferably, 2 to 4, 2 to 3, or 2), the sum of p1, p2, p3, p4 and p5 is 16 or less, the hydrogen atoms of the secondary amino groups may be each independently replaced with an alkyl group that may have an amino group, and at least one of the hydrogen atoms of the primary amino groups at both ends may be replaced with an alkyl group.],

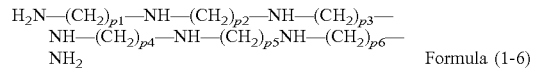

$H_2N-(CH_2)_{p1}-NH-(CH_2)_{p2}-NH-(CH_2)_{p3}-NH-(CH_2)_{p4}-NH-(CH_2)_{p5}NH-(CH_2)_{p6}-NH_2$   Formula (1-6)

[In Formula (1-6), p1, p2, p3, p4, p5, and p6 are each independently an integer from 2 to 5 (preferably, 2 to 4, 2 to 3, or 2), the sum of p1, p2, p3, p4, p5, and p6 is 15 or less, each of the hydrogen atoms of the secondary amino groups may independently be replaced with an alkyl group that may have an amino group, and at least one of the hydrogen atoms of the primary amino groups at both ends may be replaced with an alkyl group.].

In Formulae (1-2) to (1-6), the number of carbon atoms of the "alkyl group that may have an amino group" that can bond to the nitrogen atom of the secondary amino group is, for example, 1 to 6, preferably 1 to 5, preferably 1 to 4, and preferably 1 to 3. In Formulae (1-1) to (1-6), the number of carbon atoms of the "alkyl group" that can bond to the nitrogen atom of the primary amino groups at both ends is, for example, 1 to 6, preferably 1 to 5, preferably 1 to 4, and preferably 1 to 3. These "alkyl groups" are preferred to be linear or branched chain.

Examples of the polyamine represented by Formula (1) include ethylenediamine, N-ethylethylenediamine, diethylenetriamine, N-ethyldiethylenetriamine, triethylenetetramine, and tetraethylenepentamine. Besides them, the following polyamines are included: 3,3'-diaminodipropylamine; 1,3-diaminopropane; norspermidine; homospermidine; aminopropylcadaverine; aminobutylcadaverine; norspermine; thermospermine; aminopropylhomospermidine; canavalmine; homospermine; aminopentylnorspermidine; N,N-bis(aminopropyl)cadaverine; caldopentamine; homocaldopentamine; thermopentamine; caldohexamine; homocaldohexamine; thermohexamine; homothermohexamine; $N^4$-aminopropylnorspermidine; $N^4$-aminopropylspermidine; and $N^4$-aminopropylnorspermine.

In one embodiment, the nitrogen-containing compound is the primary aliphatic amine represented by Formula (2) or the secondary aliphatic amine represented by Formula (3).

$NH_2R^5$   Formula (2)

[In Formula (2), $R^5$ is a saturated or unsaturated aliphatic hydrocarbon group having 1 to 12 carbon atoms.], $NHR^6R^7$   Formula (3)

[In Formula (3), $R^6$ and $R^7$ are each independently a saturated or unsaturated aliphatic hydrocarbon group having 1 to 12 carbon atoms.].

In the aliphatic amine represented by Formula (2) or (3), the aliphatic hydrocarbon group is preferred to be a linear or branched chain aliphatic hydrocarbon group, and is preferably a linear or branched chain saturated aliphatic hydrocarbon group. The number of carbon atoms of the aliphatic hydrocarbon group is preferably 1 to 8, preferably 1 to 6, and preferably 1 to 4.

Specific examples of the aliphatic amine include: monoalkylamines, such as ethylamine, propylamine, butylamine, pentylamine, hexylamine, heptylamine, octylamine, nonylamine, and decylamine; and dialkylamines, such as diethylamine, dipropylamine, dibutylamine, diheptylamine, dioctylamine, and dicyclohexylamine.

Examples of the nitrogen-containing compound include ethylamine, ethylenediamine, diethylamine, N-ethylethylenediamine, diethylenetriamine, N-ethyldiethylenetriamine, triethylenetetramine, or tetraethylenepentamine. Among these, ethylenediamine, diethylenetriamine, triethylenetetramine, or tetraethylenepentamine is preferred. The nitrogen-containing compound is commercially available or can be manufactured by a known method or an equivalent method thereof.

The water-insoluble carrier to which the nitrogen-containing compound binds encompasses both a water-insoluble carrier to which the above-described nitrogen-containing compound directly binds covalently and a water-insoluble carrier to which the above-described nitrogen-containing compound indirectly binds via a linker. The water-insoluble carrier to which the nitrogen-containing compound binds also encompasses one to which two or more kinds of nitrogen-containing compounds that are mutually different selected from the above-described polyamine and the above-described aliphatic amine bind.

When the polyamine represented by Formula (1) is used as the nitrogen-containing compound, a plurality of amino groups may bind to the water-insoluble carrier to form a cross-linkage structure. That is, when the polyamine represented by Formula (1) is bound to the water-insoluble carrier as the nitrogen-containing compound, at least two amino groups in the polyamine binding to the water-insoluble carrier forms the cross-linkage structure. As an example, an exemplary structure obtained when diethylenetriamine (hereinafter, also referred to as DETA), a representative compound of the polyamine represented by Formula (1), is immobilized on the water-insoluble carrier is illustrated in FIG. 1. In the example in FIG. 1, N-methylol-α-chloroacetamide (hereinafter, also referred to as NMCA) is used as a linker. As illustrated in FIG. 1, among the amino groups of the diethylenetriamine, the cross-linkage structure can be obtained when both terminal primary amino groups are reacted, one terminal primary amino group and a secondary amino group are reacted, and all the amino groups (both the terminal primary amino groups and a secondary amino group) are reacted.

The "immunosuppressive protein" means a protein that functions to suppress an immune system, and its examples include a TGF-β, a LAP-bound TGF-β, an immunosuppressive acidic protein, carcinoembryonic antigen, indoleamine oxygenase (indoleamine 2,3-dioxygenase: IDO), inducible nitric oxide synthase (iNOS), arginase (ARG), interleukin 4, interleukin 6, interleukin 10, interleukin 13, and a tumor necrosis factor. Among these, the adsorption material according to the embodiment is preferred to selectively adsorb the TGF-β and the LAP-bound TGF-β from blood in terms of maximizing an effectiveness of treatment that aims regression of tumor and suppression of cancer progression of a cancer patient. It should be noted that "selectively adsorb" means that, when a liquid (for example, blood or a blood cell mixture) that contains the immunosuppressive protein (for example, the TGF-β or the LAP-bound TGF-β) is passed through a column filled with the adsorption material, a concentration of the immunosuppressive protein in the liquid that has passed through decreases compared with that before the passing, and an abundance proportion of the immunosuppressive protein in the adsorbed protein increases compared with that before the passing.

The "water-insoluble carrier" means a carrier that does not change its shape when it is immersed in water having a normal temperature (25° C.), specifically, it is preferred to be a carrier having a weight change of 5% or less when it is immersed in the water of 25° C. for one hour. Examples of the water-insoluble carrier material are not specifically limited, but preferably include polyaromatic vinyl compounds typified by polystyrenes, polyethersulfones, polysulfones, polyarylethersulfones, polyetherimides, polyimides, polyamides, and polyphenylene sulfides. The material of the water-insoluble carrier is commercially available or can be manufactured by a known method or an equivalent method thereof. These materials are materials that do not substantially have a hydroxyl group that is said to easily activate complement when contacting blood. Among these, polystyrenes are preferred because they have many aromatic rings per unit weight and an amino group is easily immobilized to polystyrenes. These polymer materials may be used alone or may be used in combination of a plurality of kinds. The water-insoluble carrier is preferred to be a polymer material comprising a polyaromatic vinyl compound (for example, a polystyrene). The water-insoluble carrier is preferred to be a copolymer of a polystyrene and a polyolefin (for example, a copolymer of a polystyrene and a polyethylene or a copolymer of a polystyrene and a polypropylene) in that it is easy to introduce a linker, such as an active halogen group, for immobilizing an amino group to a polystyrene part and in terms of easy handling and chemical resistance due to strength reinforcement by a polyolefin part. The polymer material may be one that is blended or alloyed, and in particular, a polymer alloy of a polystyrene and a polyolefin (for example, a polymer alloy of a polystyrene and a polyethylene or a polymer alloy of a polystyrene and a polypropylene) is preferred from the standpoint that it has chemical resistance and easily retains its physical shape. Among these, the polymer alloy of a polystyrene and a polypropylene that has a proven use in a blood extracorporeal circulation therapy is preferred. It is preferred that the used water-insoluble carrier does not substantially have an amino group.

The nitrogen-containing compound may directly bind to the water-insoluble carrier or may indirectly bind to the water-insoluble carrier via a linker. Examples of a method that binds the nitrogen-containing compound to the water-insoluble carrier are not particularly limited, and includes a method that covalently binds the nitrogen-containing compound to a surface of the water-insoluble carrier via a linker by a chemical method. For example, a reactive functional group can be used as a linker. As a linker, it is preferred to be one that has an electrically neutral chemical bond, such as an amide bond, a urea bond, an ether bond, or an ester bond, and preferred to be one that has the amide bond or the urea bond. Examples of the reactive functional group as the linker can include an active halogen group, such as a halomethyl group, a haloacetyl group, a haloacetamidomethyl group, or a halogenated alkyl group, an epoxy group, a carboxyl group, an isocyanate group, a thioisocyanate group, or an acid anhydride group. Among these, the active halogen group (in particular, the haloacetyl group) is preferred because it is easily manufactured, has appropriately high reactivity, can perform an immobilizing reaction of the amino group in a mild condition, and generates a chemically stabilized covalent bond. As specific examples of the polymer to which the reactive functional group is introduced include a polystyrene to which a chloroacetamidomethyl group is added, a polysulfone to which a chloroacetamidomethyl group is added, and a polyetherimide to which a chloroacetamidomethyl group is added. It should be noted that these polymers are soluble in an organic solvent, thereby having an advantage of easy molding. While a rough indication of additive amount of nitrogen-containing compound depends on a structure of the linker, it is, for example, 10 to 10,000 µmol per 1 g of water-insoluble carrier. The nitrogen-containing compound may be used in an excessive amount.

Preliminarily reacting the reactive functional group with the water-insoluble carrier ensures the reactive functional group introduced in the water-insoluble carrier. For example, when the water-insoluble carrier is a polystyrene and the reactive functional group is a chloroacetamidomethyl group, reacting the polystyrene with N-methylol-α-chloroacetamide ensures obtaining the polystyrene to which the chloroacetamidomethyl group is added.

The total content of amino groups on the water-insoluble carrier is more than 0 µmol and 2500 µmol or less per 1 g of adsorption material. The total content of amino groups is, for example, 10 µmol or more, 20 µmol or more, 30 µmol or more, 40 µmol or more, 50 µmol or more, 100 µmol or more, 200 µmol or more, 300 µmol or more, 400 µmol or more, 500 µmol or more, or 600 µmol or more per 1 g of adsorption material. The total content of amino groups is, for example, 2400 µmol or less, 2300 µmol or less, 2200 µmol or less, 2100 µmol or less, 2000 µmol or less, 1700 µmol or less, or 1500 µmol or less per 1 g of adsorption material. Any of the exemplary lower limit values can be combined with any of the exemplary upper limit values. For example, the total content of amino groups is, for example, more than 0 µmol and 2400 µmol or less, 10 µmol or more and 2400 µmol or less (10 to 2400 µmol), 20 µmol or more and 2400 µmol or less (20 to 2400 µmol), and 30 µmol or more and 2400 µmol or less (30 to 2400 µmol) per 1 g of adsorption material. When no amino group that can effectively interact with the immunosuppressive protein on the water-insoluble carrier exist at all, an adsorption performance lowers. When the total content of amino groups exceeds 2500 µmol per 1 g of adsorption material, the adsorption performance lowers. This is presumed due to the following reason. A surface charge distribution of a protein is not uniform, and the protein partially has a positive electric charge and a negative electric charge. Therefore, when an immobilization density of the amino group positively charged in the liquid is high, this causes electrostatic repulsion with the positively charged region of the protein surface, and as a result, the protein is difficult to be adsorbed on the surface. It should be noted that this presumption does not limit the embodiment.

The total content of amino groups on the water-insoluble carrier can be obtained as, for example, a sum of a content of primary amino groups, a content of secondary amino groups, a content of tertiary amino groups, and a content of quaternary amino groups (quaternary ammonium groups) by measuring the amino groups using an acid-base back titration. That is, first, the adsorption material and an excessive amount of sodium hydroxide aqueous solution are added in a polypropylene container, and are sufficiently stirred at room temperature, and the amino groups to which a salt is added in the adsorption material is desalinated. Next, the adsorption material is sufficiently cleaned until the solution becomes neutral with an ion exchanged water, and is dried until the weight change becomes 1% or less. Next, the amino groups in the dried adsorption material are reacted with a constant amount of a standard solution containing excessive acid. Next, the amount of acids remained without reacting with the amino groups is titrated with the standard solution containing a base. This method ensures obtaining the total content (µmol) of amino groups. Even more specifically, the total content of amino groups on the water-insoluble carrier can be obtained by a method described in the following examples.

The content of primary amino groups on the water-insoluble carrier is 450 µmol or less per 1 g of adsorption material, preferably 400 µmol or less, preferably 350 µmol or less, preferably 300 µmol or less, preferably 250 µmol or less, and preferably 200 µmol or less. When the primary amino groups are more than 450 µmol per 1 g of adsorption material, hydrophilicity of the carrier in the liquid increases to lower the physical strength of the carrier, thereby easily generating microparticles. It should be noted that the above-described preferred total content of amino groups on the water-insoluble carrier and the above-described preferred content of primary amino groups on the water-insoluble carrier can be conveniently combined.

The content of primary amino groups can be controlled by, for example, adjusting a binding amount of the reactive functional groups to the water-insoluble carrier, a kind of nitrogen-containing compound, and a usage of the nitrogen-containing compound. The binding amount of the reactive functional groups can be controlled by, for example, reactive conditions, such as a kind of reactive functional group or a kind of solvent, an immersing temperature, or an immersing period. For example, when the water-insoluble carrier contains the polyaromatic vinyl compound, a binding position of the reactive functional group can also be controlled using a crosslinking agent. An immobilizing amount of nitrogen-containing compound can be controlled by reactive conditions, such as a kind of solvent, an immersing temperature, and an immersing period, in addition to the kind of nitrogen-containing compound and the binding amount of the reactive functional groups.

The content of primary amino groups on the water-insoluble carrier can be, for example, measured by back titrating the primary amino groups in the adsorption material using o-phthalaldehyde (hereinafter, OPA) that generates a fluorescent molecule by specifically reacting with the primary amino groups in the presence of a thiol compound. That is, first, the dried adsorption material is disposed in a polypropylene container. An excessive OPA and dithiothreitol (hereinafter, DTT) of the thiol compound are dissolved in 80 volume % of methanol and 20 volume % of carbonate pH standard liquid (pH 10.01) to prepare a mixed solution. The mixed solution is added into the polypropylene container in which the above-described adsorption material is disposed, and is sufficiently stirred at room temperature. After stirring, the solution is collected to be a measurement sample. A mixed solution is prepared as a sample for calibration curve such that OPA, DTT, 80 volume % of methanol, and 20 volume % of carbonate pH standard liquid (pH 10.01) are added to have known concentrations. The measurement sample and the sample for calibration curve are mixed with carbonate pH standard liquids (pH 10.01) containing n-propylamine and DTT to obtain the measurement sample after dilution and the sample for calibration curve after dilution. After a certain period of time, absorbances at 340 nm are measured for the measurement sample after dilution and the sample for calibration curve after dilution with a spectrophotometer, and comparing them ensures calculating the content (μmol) of primary amino groups on the water-insoluble carrier. Specifically, the content of primary amino groups on the water-insoluble carrier can be obtained by a method described in the following example.

A proportion of the content of primary amino groups to the total content of amino groups per 1 g of adsorption material (content of primary amino groups/total content of amino groups) is preferably 0.30 or less, preferably 0.25 or less, and preferably 0.20 or less.

A "diameter of fiber" can be obtained by the following method. First, a hundred samples of fibers are randomly extracted, and one photograph of a cross-sectional surface (a cross-sectional surface perpendicular to the extension direction of the fiber) is taken for each one sample at 1000 to 3000-fold magnification using a scanning electron microscope. Next, the diameters of the respective fiber cross-sectional surfaces are measured. Calculating a mean value of those values (a mean value of the diameters of total of a hundred cross-sectional surfaces) obtains the "diameter of fiber." When the fiber cross-sectional surface is not a circle, a diameter of a circle that has the same area as the cross-sectional area is the diameter of fiber.

A "diameter of particle" can be obtained by the following method. First, ten sample groups of particles are randomly extracted, and one photograph is taken for each one sample group at 1000 to 3000-fold magnification using a scanning electron microscope. Next, diameters of ten particles per one photograph are measured. Calculating a mean value of those values (a mean value of the diameters of total of a hundred particles) obtains the "diameter of particle." When a pictured shape of the particle is not a circle, a diameter of a circle that has the same area as the particle area is the diameter of particle.

Setting the diameter of fiber or particle to 15 μm or more ensures appropriately reducing a packing density of the adsorption material to the column, and as a result, various kinds of cells, such as a platelet and a leukocyte, are difficult to be adsorbed to the fiber or the particle. Among the leukocytes, a granular leukocyte and a mononuclear leukocyte have phagocytic activities, and therefore, setting the diameter of fiber or particle to 15 μm or more makes the fiber or the particle difficult to be detected as foreign matter, and as a result, the leukocyte is difficult to be adsorbed to the fiber or the particle. When the diameter of fiber or particle is 50 μm or less, the packing density of the adsorption material to the column appropriately improves. Therefore, a blood contact area per unit volume of the adsorption material increases, and as a result, an amount of absorption of the immunosuppressive protein can be improved. Because of the above-mentioned reasons, the diameter of fiber or particle that constitutes the water-insoluble carrier is preferably 15 μm or more and 50 μm or less (15 to 50 μm), preferably 16 μm or more and 40 μm or less (16 to 40 μm), and preferably 17 μm or more and 35 μm or less (17 to 35 μm). Any of the preferred lower limit values can be combined with any of the preferred upper limit values.

An "arithmetic mean roughness" means a mean value of absolute values of deviations from an average line to a measurement curved line of an extracted part that is extracted by a reference length L in the direction of the average line from a roughness curved line, and means an arithmetic mean roughness (Ra) in Japanese Industrial Standard B 0601-2001. The arithmetic mean roughness can be measured with, for example, a shape measurement laser microscope. For the measurement environment, it is preferred that the measurement be performed with the water-insoluble carrier being wet with water. In the case where there is an orientation as with a fiber, a value in the longitudinal direction is measured.

When the arithmetic mean roughness of a surface of the water-insoluble carrier is 3.0 μm or less, the granular leukocyte and the mononuclear leukocyte having the phagocytic activities have difficulty in detecting unevenness of the water-insoluble carrier as foreign matter, thereby having difficulty in being adsorbed to the surface. The adhesion induction of platelets also decreases. Therefore, the adsorption performance of the immunosuppressive protein can be improved. Meanwhile, when the arithmetic mean roughness of the surface of the water-insoluble carrier is 0.1 μm or more, the adsorption performance of the immunosuppressive protein can be improved. It is presumed that this is because an area where the immunosuppressive protein can be in contact with the material surface increases. From the above-mentioned reasons, the arithmetic mean roughness of the surface of the water-insoluble carrier (or the adsorption material) is preferably 0.1 μm or more and 3.0 μm or less (0.1 to 3.0 μm), and preferably 0.5 μm or more and 2.0 μm or less (0.5 to 2.0 μm). Any of the preferred lower limit values can be combined with any of the preferred upper limit values. It should be noted that the preferred diameter of the above-described fiber or the above-described particle and the preferred arithmetic mean roughness of the surface of the above-described water-insoluble carrier can be conveniently combined.

The arithmetic mean roughness of the surface of the water-insoluble carrier can be, for example, controlled by immersing the water-insoluble carrier in an organic solvent. Examples of methods for controlling the arithmetic mean roughness of the surface of the water-insoluble carrier include a method that a polymer obtained by mixing a polyaromatic vinyl compound and a polypropylene as a water-insoluble carrier is immersed in a solvent that can partly dissolve the polyaromatic vinyl compound and that does not dissolve the polypropylene. The arithmetic mean roughness of the surface of the water-insoluble carrier can be controlled by, for example, a kind of polymer, a molecular weight of polymer, a kind of solvent, an immersing temperature, and an immersing period. Furthermore, for the polyaromatic vinyl, introducing a crosslinking agent ensures employing a method that, for example, controls the solubility to a solvent. Furthermore, the above-described reaction can also be simultaneously performed with an introduction reaction of the nitrogen-containing compound.

Exemplary forms of the water-insoluble carrier include a fiber, a particle, or their high-order processed product. Among them, the fiber is preferred in that the fiber can have an increased area in contact with blood while securing a blood flow passage by high-order processing. Among them, a sea-island type composite fiber is preferred, and from a standpoint of retaining strength as a material, a sea-island type composite fiber whose island is a reinforcing material and sea is an alloy of a water-insoluble polymer and a reinforcing material is preferred, and furthermore, a sea-island type composite fiber in which island is a polypropylene and sea is an alloy of a polystyrene and a polypropylene is preferred.

Examples of the reinforcing material are not specifically limited, and include polyamides, polyacrylonitriles, polyethylenes, polypropylenes, nylons, polymethyl methacrylates, and polytetrafluoroethylenes. Among these, polypropylenes are preferred. These polymers may be used alone or may be used in combination of a plurality of kinds.

When the form of the water-insoluble carrier is the fiber, the water-insoluble carrier is preferred to be a knitted fabric as a high-order processed product. The knitted fabric can secure a blood flow passage by controlling its stitch, and therefore, using the knitted fabric ensures reducing a pressure loss when blood passes through the fiber. When the knitted fabric is formed by doubling the fibers, the number of doublings is preferably 10 or more and 100 or less, and preferably 30 or more and 80 or less. Setting the number of doublings to 100 or less causes blood to easily and efficiently be in contact with the fibers in a deep portion of the fiber bundle, thereby improving an amount of absorption of the immunosuppressive protein. Setting the number of doublings to 10 or more improves maintainability of the knitted fabric. Any of the preferred lower limit values can be conveniently combined with any of the preferred upper limit values.

The adsorption material of the embodiment can be used for an adsorption carrier for the immunosuppressive protein (in particular, the TGF-β or the LAP-bound TGF-β), and can be used as a filler of the adsorption column.

In the embodiment, the amount of absorption of TGF-β or LAP-bound TGF-β per 1 g of adsorption material is preferably 7.0 ng or more, preferably 10.0 ng or more, and preferably 11.0 ng or more. Exemplary test systems of the amount of absorption of the adsorption material include a batch adsorption test using a TGF-β solution, and exemplary evaluation systems include an analysis by Enzyme-Linked ImmunoSorbent Assay (hereinafter, ELISA method).

Furthermore, in consideration of extracorporeal circulation usage, the amount of microparticles generated by a separation of a part of the adsorption material is desired to be smaller Accordingly, the number of microparticles generated from the adsorption material is preferred to be as few as possible. When the physical strength of the adsorption material is retained, the number of microparticles generated from the adsorption material is decreased. Meanwhile, when the physical strength of the adsorption material lowers, the number of microparticles generated from the adsorption material is increased. Exemplary test systems that examine the microparticle generation from the adsorption material include General Tests, Processes, and Apparatus, 6.07 Insoluble Particulate Matter Test for Injections in The Japanese Pharmacopoeia, Fifteenth Edition (Mar. 31, 2006, the Ministry of Health, Labour and Welfare Ministerial Notification No. 285), and exemplary evaluation systems include a method that measures the number (count) of generated microparticles with a light obscuration automatic particle counter.

In consideration of extracorporeal circulation usage, the amount of a blood anticoagulant adsorbed to the adsorption material is desired to be smaller. Generally, before performing the extracorporeal circulation, in order to prevent blood from coagulating in the column, which is caused by the blood anticoagulant dissolved in the blood being adsorbed by the adsorption material during the extracorporeal circulation, a normal saline in which the blood anticoagulant is dissolved is passed through the blood purification column filled with the adsorption material to cause the blood anticoagulant to be preliminarily adsorbed to the adsorption material. When the amount of the blood anticoagulant preliminarily adsorbed to the adsorption material is small, a usage of the blood anticoagulant can be reduced, and also the possibility of an excessive leakage of the blood anticoagulant adsorbed to the adsorption material once into the blood can be lowered. Examples of the blood anticoagulant are not specifically limited, and include heparin, sodium citrate, mesylate, sodium fluoride, and EDTA-2K. Among these, the heparin is preferred. Exemplary evaluation methods for an adsorption rate of blood anticoagulant with the adsorption material include a batch adsorption test that uses the normal saline in which the blood anticoagulant is dissolved. When the blood anticoagulant is the heparin, an analysis by a colorimetric assay method using a spectrophotometer can be preferably used. That is, the adsorption material and the normal saline in which the heparin is dissolved are added in a polypropylene container, and are mixed by inverting for two hours in an incubator at 37° C. After mixing, the solution is collected to be a measurement sample. As a sample for calibration curve, a heparin normal saline is prepared to have an already-known concentration. Absorbances at 210 nm are measured with a spectrophotometer for the measurement sample and the sample for calibration curve, and comparing them ensures calculating a heparin concentration in the measurement sample. The adsorption rate of the heparin with the adsorption material can be calculated as a percentage of a value obtained by dividing a value obtained by subtracting the heparin concentration after the incubation from the heparin concentration before the incubation by the heparin concentration before the incubation. Specifically, the adsorption rate of the heparin with the adsorption material can be obtained by a method described in the following example.

From a standpoint of the adsorption rate of the blood anticoagulant, the total content of amino groups on the water-insoluble carrier per 1 g of adsorption material is preferably 1800 μmol or less, preferably 1000 μmol or less, preferably 700 μmol or less, preferably 600 μmol or less, preferably 500 μmol or less, preferably 400 μmol or less, preferably 300 μmol or less, preferably 250 μmol or less, and preferably 150 μmol or less. From a standpoint of the adsorption rate of the blood anticoagulant, the content of primary amino groups on the water-insoluble carrier per 1 g of adsorption material is preferably 400 μmol or less, preferably 200 μmol or less, preferably 100 μmol or less, preferably 75 μmol or less, preferably 50 μmol or less, and preferably 30 μmol or less.

The adsorption column of the embodiment includes the adsorption material of the embodiment.

The "adsorption column" means one that has at least a blood inlet portion, a housing portion, and a blood outlet portion, and the housing portion is filled with the adsorption material. Exemplary adsorption columns include a radial flow type adsorption column. As described above, the form of the adsorption material is preferably a fiber, and preferably a knitted fabric.

Figure 2:
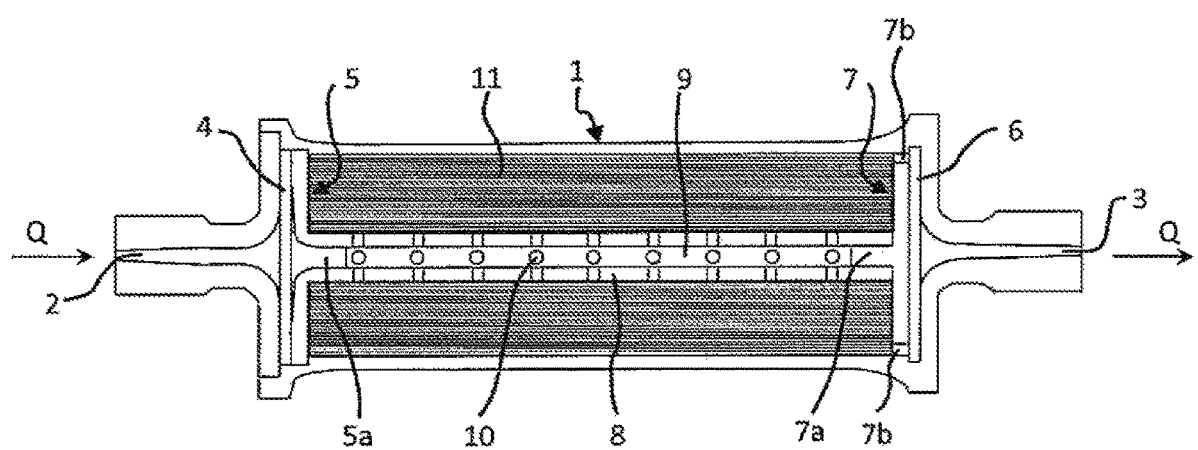
FIG. 2 is a vertical cross-sectional view of an exemplary radial flow type adsorption column.

An exemplary configuration of an inside of the adsorption column will be described along FIG. 2. In FIG. 2, reference numeral 1 denotes a container body, and there are an inflow port 2 and an outflow port 3 at a front end and a rear end in its longitudinal direction. The inflow port 2 has an inside where a filter 4 and a circular plate-shaped partition plate 5 are disposed. The outflow port 3 has an inside where a filter 6 and a circular plate-shaped partition plate 7 are disposed. Among the two partition plates 5 and 7, the partition plate 5 in the front side (inflow port side) has an opening 5a in the center, and the partition plate 7 in the rear side has a center portion where a support protrusion 7a is disposed. The partition plate 7 has an outer periphery where multiple through holes 7b are intermittently provided in the circumferential direction. Furthermore, one pipe 8 is bridged between the opening 5a of the partition plate 5 and the support protrusion 7a of the partition plate 7. The pipe 8 internally has a flow passage 9 that introduces blood and has a peripheral wall on which multiple through-holes 10 are provided. The pipe 8 has its front end communicating with the opening 5a of the partition plate 5 and has its rear end closed with the support protrusion 7a of the partition plate 7. The outer periphery of this pipe 8 is wound with a plurality of layers of an adsorption material 11 for many times. When this adsorption column is used for a circulation method, tubes are coupled to the inflow port 2 and the outflow port 3 that forms a circulation circuit with a blood pool. The blood taken out of the blood pool is supplied to the inflow port 2, a target adsorption substance (the immunosuppressive protein) is removed with the adsorption material 11 inside, and the blood is flown out of the outflow port 3 to circulate the blood so as to return to the blood pool again. In the column, the blood that entered the flow passage 9 through the filter 4 from the inflow port 2 moves through the flow passage 9 and sequentially infiltrates into the adsorption material 11 from the through-holes 10 to move to any of the radial directions while cells and the like are adsorbed. The blood from which the cells and the like are removed flows out of the multiple through holes 7b on the outer periphery of the partition plate 7, and flows out of the outflow port 3 through the filter 6. While in the above-described example, the blood flows out of the through-holes 10 while flowing through the flow passage 9 inside the pipe 8 from the opening 5a, the moving direction of the blood in the adsorption column may be inverted from the above to supply the blood from the outflow port 3 and be flown out of the inflow port 2.

In order to increase adsorption efficiency of the immunosuppressive protein, a blood linear velocity in the column is also important. That is, when the blood linear velocity is fast, there may be a case where a sufficient interaction of the immunosuppressive protein with the adsorption material becomes difficult to happen. Meanwhile, when the blood linear velocity is slow, there may be a case where other blood components, such as a platelet and a leukocyte, non-specifically adhere to the adsorption material to inhibit the interaction between the adsorption material and the immunosuppressive protein. Accordingly, the maximum value of blood linear velocity in the adsorption material when a flow rate of the adsorption column inlet is 50 cm³/minute is preferably 50 cm/minute or less, and preferably 25 cm/minute or less. The minimum value of blood linear velocity in the adsorption material when the flow rate of the adsorption column inlet is 50 cm³/minute is preferably 0.1 cm/minute or more and preferably 0.3 cm/minute or more. Here, the blood linear velocity is obtained by a calculation, and, for example, in the case of a radial flow type adsorption column, the maximum value ($V_{max}$) of the blood linear velocity in the adsorption material is calculated from a total area ($S_p$) of the openings that open on the side surface of the center pipe in a hollow columnar shape and the flow rate (50 cm³/minute) of the adsorption column inlet by the following Formula 1.

$$V_{max}(\text{cm/minute})=50(\text{cm}^3/\text{minute})/S_p(\text{cm}^2) \quad \text{Formula 1}$$

The minimum value ($V_{min}$) is calculated from an area ($S_o$) of an outermost peripheral surface of the adsorption material wound around the center pipe and the flow rate (50 cm³/minute) of the adsorption column inlet by the following Formula 2.

$$V_{min}(\text{cm/minute})=50(\text{cm}^3/\text{minute})/S_o(\text{cm}^2) \quad \text{Formula 2}$$

Meanwhile, when the adsorption column is an adsorption column in a columnar shape made of particles or made by simply stacking fibers, the minimum value and the maximum value of the cross-sectional area of the adsorption material perpendicular to the blood flow are the same, and therefore, the above-described maximum value ($V_{max}$) and the above-described minimum value ($V_{min}$) are the same values.

Furthermore, the adsorption column is preferred to be a radial flow type adsorption column that includes a center pipe, a plate A, and a plate B. The center pipe has a side surface in the longitudinal direction where through-holes are provided for flowing out the supplied blood. The adsorption material is filled around the above-described center pipe. The plate A is communicated through the upstream end of the above-described center pipe for causing the above-described blood that flows in to pass inside the above-described center pipe and is disposed to prevent the above-described blood from contacting the adsorption material without passing through the center pipe. The plate B is disposed to close the downstream end of the above-described center pipe and secure the adsorption material in a space around the above-described center pipe. This causes the blood to uniformly flow through the adsorption material. It should be noted that when an aperture ratio of the through-holes of the above-described center pipe is low, the pressure loss easily occurs in this part, and therefore, granular leukocytes, mononuclear leukocytes, and platelets are activated so that they adhere easily to the adsorption material. Therefore, there may be a case where the adsorption performance of the immunosuppressive protein lowers. When the aperture ratio is high, it is possible to have problems, such as reduced strength of the pipe and easy occurrence of a short path at the through-holes near the blood inlet portion. Accordingly, the aperture ratio of the through-holes is preferably 20 to 80%, and preferably 30 to 60%.

The "radial flow type" means the way the blood flows inside the column. When the blood is flown in the perpendicular direction to the inlet and the outlet of the column, and there is the blood flow in the horizontal direction inside the column, it is referred to as a radial flow type.

The "aperture ratio of through-holes" means a value obtained by the following Formula 3.

$$\text{Aperture ratio of through-holes (\%)}=\text{sum of areas of through-holes formed on side surface in longitudinal direction of pipe/area of side surface of pipe}\times 100 \quad \text{Formula 3}$$

As described above, the adhesion of the platelets is a cause of the reduced amount of absorption of the immunosuppressive protein and also causes clogging of the column, and therefore, it is desired that the platelets adhere to the adsorption material as less as possible. Accordingly, the adhesion rate of the platelets to the adsorption material is preferably 80% or less, preferably 70% or less, and preferably 65% or less. The adhesion rate of the platelets can be, for example, evaluated by a batch test using a blood cell counter.

The adsorption column of the embodiment can be used in a blood purification therapy. Using the adsorption column of the embodiment as a column for blood purification ensures efficiently removing the immunosuppressive protein from blood. For example, extracorporeally circulating blood and passing the blood through the adsorption column of the embodiment ensures efficiently removing the immunosuppressive protein from the blood. That is, the adsorption column of the embodiment can be used as a column for extracorporeal circulation. More specifically, the adsorption column of the embodiment can be used for a therapy that selectively removes the immunosuppressive protein from blood of a cancer patient. That is, the adsorption column of the embodiment can be used as a column for cancer therapy.

The adsorption column of the embodiment is appropriately used for cancer therapy since it can adsorb the immunosuppressive protein. It is also possible to use in combination with a cell infusion treatment that activates dendritic cells, natural killer cells, and the like.

EXAMPLES

While the following describes the embodiment with examples, the embodiment is not limited to these examples.
1. Manufacturing Immunosuppressive Protein Adsorption Material As a water-insoluble carrier, a sea-island type composite fiber (diameter of 20 μm) that has 16 islands of island component made of polypropylene (Prime Polymer Co., Ltd.; J105WT) and a sea component made of 90 weight % of polystyrene (weight average molecular weight: 181,000) and 10 weight % of polypropylene (Prime Polymer Co., Ltd.; J105WT), while a ratio of the island and the sea (weight ratio) was 50:50. The obtained 42 fibers were combined to form a knitted fabric (hereinafter, a raw knitted fabric 1). It should be noted that a roughness of a fiber surface is affected by the number of islands, a sea/island ratio, molecular weights of polystyrene and polypropylene, and the like.

Two grams of paraformaldehyde (hereinafter, PFA) was dissolved in a mixed solution of 20 mL of nitrobenzene and 13.3 mL of sulfuric acid at 10° C. (hereinafter, a PFA solution). Furthermore, 46.9 g of N-methylol-α-chloroacetamide was dissolved in a mixed solution of 259.3 mL of nitrobenzene and 169.3 mL of sulfuric acid at 10° C. (hereinafter, an NMCA solution). After immersing 10 g of the raw knitted fabric 1 in the PFA solution, the NMCA solution was promptly added and stirred. After immersion for two hours under stirring, the knitted fabric was taken out. After cleaning with excessive nitrobenzene, the knitted fabric was displaced and cleaned with methanol, and further cleaned with water, to obtain an α-chloracetamidomethylated knitted fabric (hereinafter, an intermediate 1). A series of operation from the manufacturing of the PFA solution to the cleaning of the knitted fabric using the methanol was performed at 15° C. or less.

(1) Manufacturing Immunosuppressive Protein Adsorption Material 1-1

The intermediate 1 (10 g) was dipped in a solution in which diethylenetriamine (46 ∞L) and triethylamine (28.6 mL) were dissolved in dimethylsulfoxide (398 mL), and was stirred for three hours at 40° C. Afterwards, the intermediate 1 processed with the diethylenetriamine was cleaned with water and dried, to obtain an immunosuppressive protein adsorption material 1-1.

(2) Manufacturing Immunosuppressive Protein Adsorption Material 1-2

Similarly to the immunosuppressive protein adsorption material 1-1, an immunosuppressive protein adsorption material 1-2 was obtained.

(3) Manufacturing Immunosuppressive Protein Adsorption Material 2-1

Except that an amount of diethylenetriamine was 232 μL, an immunosuppressive protein adsorption material 2-1 was obtained similarly to the immunosuppressive protein adsorption material 1-1.

(4) Manufacturing Immunosuppressive Protein Adsorption Material 2-2

Similarly to the immunosuppressive protein adsorption material 2-1, an immunosuppressive protein adsorption material 2-2 was obtained.

(5) Manufacturing Immunosuppressive Protein Adsorption Material 3

Except that an amount of diethylenetriamine was 464 μL, an immunosuppressive protein adsorption material 3 was obtained similarly to the immunosuppressive protein adsorption material 1-1.

(6) Manufacturing Immunosuppressive Protein Adsorption Material 4-1

Except that an amount of diethylenetriamine was 929 μL, an immunosuppressive protein adsorption material 4-1 was obtained similarly to the immunosuppressive protein adsorption material 1-1.

(7) Manufacturing Immunosuppressive Protein Adsorption Material 4-2

Similarly to the immunosuppressive protein adsorption material 4-1, an immunosuppressive protein adsorption material 4-2 was obtained.

(8) Manufacturing Immunosuppressive Protein Adsorption Material 5

Except that ethylenediamine (929 μL) was used instead of the diethylenetriamine (46 μL), an immunosuppressive protein adsorption material 5 was obtained similarly to the immunosuppressive protein adsorption material 1-1.

(9) Manufacturing Immunosuppressive Protein Adsorption Material 6

Except that tetraethylenepentamine (1,863 μL) was used instead of the diethylenetriamine (46 μL), an immunosuppressive protein adsorption material 6 was obtained similarly to the immunosuppressive protein adsorption material 1-1.

(10) Manufacturing Immunosuppressive Protein Adsorption Material 7-1

Except that an amount of diethylenetriamine was 1,863 μL, an immunosuppressive protein adsorption material 7-1 was obtained similarly to the immunosuppressive protein adsorption material 1-1.

(11) Manufacturing Immunosuppressive Protein Adsorption Material 7-2

Similarly to the immunosuppressive protein adsorption material 7-1, an immunosuppressive protein adsorption material 7-2 was obtained.

(12) Manufacturing Immunosuppressive Protein Adsorption Material 8-1

Except that an amount of diethylenetriamine was 4,687 μL, an immunosuppressive protein adsorption material 8-1 was obtained similarly to the immunosuppressive protein adsorption material 1-1.

(13) Manufacturing Immunosuppressive Protein Adsorption Material 8-2

Similarly to the immunosuppressive protein adsorption material 8-1, an immunosuppressive protein adsorption material 8-2 was obtained.

(14) Manufacturing Immunosuppressive Protein Adsorption Material 9

Except that an amount of diethylenetriamine was 9,479 µL, an immunosuppressive protein adsorption material 9 was obtained similarly to the immunosuppressive protein adsorption material 1-1.

(15) Manufacturing Immunosuppressive Protein Adsorption Material 10

Except that tetraethylenepentamine (4,687 µL) was used instead of the diethylenetriamine (46 µL), an immunosuppressive protein adsorption material 10 was obtained similarly to the immunosuppressive protein adsorption material 1-1.

(16) Manufacturing Immunosuppressive Protein Adsorption Material 11

Except that an amount of diethylenetriamine was 19,388 µL, an immunosuppressive protein adsorption material 11 was obtained similarly to the immunosuppressive protein adsorption material 1-1.

(17) Manufacturing Immunosuppressive Protein Adsorption Material 12

Except that an amount of diethylenetriamine was 32,964 µL, an immunosuppressive protein adsorption material 12 was obtained similarly to the immunosuppressive protein adsorption material 1-1.

(18) Manufacturing Immunosuppressive Protein Adsorption Material 13

Ten grams of the intermediate 1 was dipped in a solution in which polyethylenimine having a number average molecular weight of approximately 600 (8,195 µL) and triethylamine (28.6 mL) were dissolved in dimethylsulfoxide (398 mL), and was stirred for three hours at 40° C. Afterwards, the intermediate 1 processed with the polyethylenimine was cleaned with water and dried, to obtain an immunosuppressive protein adsorption material 13.

(19) Manufacturing Immunosuppressive Protein Adsorption Material 14

Ten grams of the intermediate 1 was dipped in a solution in which a polyethylenimine 50 weight % aqueous solution (16,390 µL) which has a number average molecular weight of approximately 750,000 and triethylamine (28.6 mL) were dissolved in dimethylsulfoxide (398 mL), and was stirred for three hours at 40° C. Afterwards, the intermediate 1 processed with the polyethylenimine was cleaned with water and dried, to obtain an immunosuppressive protein adsorption material 14.

(20) Manufacturing Immunosuppressive Protein Adsorption Material 15

Ten grams of the intermediate 1 was dipped in a solution in which a polyallylamine 20 weight % aqueous solution (2,876 µL) which has a number average molecular weight of approximately 65,000 and triethylamine (28.6 mL) were dissolved in dimethylsulfoxide (398 mL), and was stirred for three hours at 40° C. Afterwards, the intermediate 1 processed with the polyallylamine was cleaned with water and dried, to obtain an immunosuppressive protein adsorption material 15.

2. Measuring Total Content of Amino Groups Contained in Adsorption Material

The total contents of amino groups on the water-insoluble carriers for the manufactured adsorption materials and the like were measured by acid-base back titration. The adsorption material (1.0 g) and a 6 M sodium hydroxide aqueous solution (50 mL) were added in a polypropylene container, and stirred for one hour at room temperature. Next, the above-described adsorption material was added to another polypropylene container containing an ion exchanged water (50 mL), and stirred for 30 minutes at room temperature (cleaning). Repeating the cleaning until a pH of the ion exchanged water comprising the adsorption material reaches 7 provided a desalinated adsorption material. The adsorption material after the desalination was left to stand for 48 hours under decompression at 25° C. to be dried. A weight of the adsorption material after drying was measured, the adsorption material and 40 mL of 0.1 M hydrochloric acid were added to a new polypropylene container, and stirred for 30 minutes at room temperature. After stirring, 5 mL of solution only was extracted to be moved to a new polypropylene container. Next, 0.1 mL of a 0.1 M sodium hydroxide aqueous solution was dropped into the obtained solution. After dropping, the solution was stirred for 10 minutes, and a pH of the solution was measured. The dropping of the sodium hydroxide, the 10 minute stirring, and the pH measurement were similarly repeated for 100 times. The dropping amount of sodium hydroxide aqueous solution when the pH of the solution exceeded 8.5 was set to the titer. Using the titer per 1 g of adsorption material and the following Formula 4, the total content of amino groups per 1 g of adsorption material was calculated.

Total content of amino groups per 1 g of adsorption material (µmol)={liquid amount of added 0.1 M hydrochloric acid (40 mL)/liquid amount of extracted hydrochloric acid (5 mL)}×titer (mL) ÷weight of adsorption material after drying (g)× sodium hydroxide aqueous solution concentration (0.1 M)       Formula 4

3. Measuring Content of Primary Amino Groups Contained in Adsorption Material The content of primary amino groups on the water-insoluble carrier was measured using o-phthalaldehyde (hereinafter, OPA) that generates a fluorescent substance by specifically reacting with the primary amino group. First, the adsorption materials were punched out to be any number of circular shapes with diameters of 6 mm with a punch, and left to stand for 48 hours under decompression at 25° C. to be dried. Next, a weight of the adsorption material after drying was measured, and the adsorption material was disposed in a polypropylene container. OPA and DTT were dissolved in 80 volume % of methanol and 20 volume % of a carbonate pH standard solution (pH 10.01) to have concentrations of 1.5 mM and 5 mM, respectively, to prepare a mixed solution. The mixed solution was added into the polypropylene container in which the above-described adsorption material was disposed, and stirred for three hours at room temperature. After stirring, 100 µL of the solution was collected to be a measurement sample. As samples for calibration curve, mixed solutions containing OPA (respective concentrations were adjusted to be 0 mM, 0.375 mM, 0.75 mM, and 1.5 mM), 5 mM of DTT, 80 volume % of methanol, and 20 volume % of carbonate pH standard solution (pH 10.01) were prepared. 100 µL of measurement sample and 100 µL of sample for calibration curve were each mixed with 1 mL of carbonate pH standard solution (pH 10.01) containing 6.1 mM of n-propylamine and 5 mM of DTT to obtain the measurement sample after dilution and the sample for calibration curve after dilution. After 90 seconds, absorbances at 340 nm were measured for the measurement sample after dilution and the sample for calibration curve after dilution with a spectrophotometer. An OPA concentration of the measurement sample after dilution was obtained from the calibration curve, and multiplied by a dilution rate to convert to the OPA concentration of the measurement sample before dilution (hereinafter, a sample OPA concentration).

Using the following Formula 5, the content of primary amino groups per 1 g of adsorption material was calculated.

Content of primary amino groups per 1 g of adsorption material (μmol)={added OPA concentration (1.5 mM)−sample OPA concentration}×amount of mixed solution stirred and reacted with adsorption material (mL)/weight of adsorption material after drying (g)   Formula 5

4. LAP-bound TGF-β1 Adsorption Performance Test

LAP-bound TGF-β1 concentrations in a solution before and after an adsorption reaction in the immunosuppressive protein adsorption material were quantitatively determined by ELISA method, and an amount of absorption of the LAP-bound TGF-β1 per 1 g of material was calculated in accordance with the following Formula 6. That is, four immunosuppressive protein adsorption materials cut out into disk shapes with diameters of 6 mm were put into a polypropylene container having a capacity of 2 mL. In this container, 3.5 weight % of bovine serum albumin and 1.1 mL of phosphate buffered saline in which a concentration of recombinant human LAP-bound TGF-β1 (R&D Systems, Inc.) was adjusted to be 25 ng/mL were added, and mixed by inverting for two hours in an incubator at 37° C. After the adsorption fiber carrier was removed from the container, a residual concentration of the LAP-bound TGF-β1 in the solution was measured using Quantikine Human LAP (TGF-β1) ELISA Kit (R&D Systems, Inc.). The four immunosuppressive protein adsorption materials cut out into disk shapes with diameters of 6 mm were left to stand for 48 hours under decompression at 25° C. to be dried. A weight of the four immunosuppressive protein adsorption materials after drying was measured. An amount of absorption of the LAP-bound TGF-β1 was calculated in accordance with the following Formula 6.

Amount of absorption of LAP-bound TGF-β1 per 1 g of adsorption material={(LAP-bound TGF-β1 concentration before incubation)−(LAP-bound TGF-β1 concentration after incubation)}/(LAP-bound TGF-β1 concentration before incubation)×phosphate buffered saline amount 1.1 mL±(dry weight of four adsorption materials cut out into disk shapes with diameters of 6 mm)   Formula 6

5. Manufacturing Column Including Protein Adsorption Material as Adsorption Carrier Four grams each of the raw knitted fabric 1 or the immunosuppressive protein adsorption materials 1-1, 2-1, 3, 4-1, 5, 6, 7-1, 8-1, and 9 to 15 were filled per one radial flow type column made of polypropylene-polyethylene copolymer (diameter: 25 mm×length: 133 mm, adsorption fiber filled portion volume: 14.7 cm$^3$). Afterwards, after filling inside the column with a physiological saline, a high-pressure steam sterilization was performed, and each column including the raw knitted fabric 1 as the adsorption carrier (hereinafter, a "raw knitted fabric 1 column"), and columns including the immunosuppressive protein adsorption materials 1-1, 2-1, 3, 4-1, 5, 6, 7-1, 8-1, and 9 to 15 as the adsorption carrier (hereinafter, "columns 1 to 15") were obtained.

6. Insoluble Microparticle Count Measurement

The measurement was performed by referring to General Tests, Processes, and Apparatus, 6.07 Insoluble Particulate Matter Test for Injections (Method 1: Light Obscuration Particle Count Test; pp. 1-2) in The Japanese Pharmacopoeia, Fifteenth Edition (Mar. 31, 2006, the Ministry of Health, Labour and Welfare Ministerial Notification No. 285). By referring to the method of vibration test of packaged freights and containers (Japanese Industrial Standard Z 0232), the column was vibrated for one hour each in the horizontal and the perpendicular directions. The column after the vibration was coupled to a commercially available blood circuit for artificial kidney, and was cleaned at a flow rate of 100 mL per minute using 2 L of physiological saline. It should be noted that the physiological saline to be used was filtered with a filter having a pore size of 0.3 μm, and it was confirmed that microparticles of 10 μm or more were 0.5 count/mL or less and microparticles of 25 μm or more were 0.2 count/mL or less. The filtered physiological saline was sent into this product for one hour at a flow rate of 50 mL per minute using a pump, and 1 L of its effluent was extracted per 20 minutes in total of three times (total of 3 L). 300 mL each of the obtained effluents were supplied to a light obscuration automatic particle counter to measure the microparticles, and the number of microparticles (count/mL) after sending the liquid for one hour was calculated.

EXAMPLES 1 TO 10

The measurement of total content of amino groups, the measurement of content of primary amino groups, and the LAP-bound TGF-β1 adsorption performance test were performed for the immunosuppressive protein adsorption materials 1-1, 2-1, 3, 4-1, 5, 6, 7-1, 8-1, 9, and 10. Using columns 1 to 10, the numbers of insoluble microparticles were measured. The results are illustrated in Table 1.

It was confirmed that the immunosuppressive protein adsorption materials 1-1, 2-1, 3, 4-1, 5, 6, 7-1, 8-1, 9, and 10 had low generation amounts of insoluble microparticles and were able to efficiently adsorb the LAP-bound TGF-β1.

COMPARATIVE EXAMPLE 1

The measurement of total content of amino groups, the measurement of content of primary amino groups, and the LAP-bound TGF-β1 adsorption performance test were performed for the raw knitted fabric 1 column (the raw knitted fabric 1). Using the raw knitted fabric 1 column, the number of the insoluble microparticles was measured. The result is illustrated in Table 2.

With the raw knitted fabric 1 column (the raw knitted fabric 1), a generation amount of insoluble microparticles was low, but the LAP-bound TGF-β1 was not able to be efficiently adsorbed.

COMPARATIVE EXAMPLES 2 TO 6

The measurement of total content of amino groups, the measurement of content of primary amino groups, and the LAP-bound TGF-β1 adsorption performance test were performed for the immunosuppressive protein adsorption materials 11 to 15. Using columns 11 to 15, the numbers of the insoluble microparticles were measured. The results are illustrated in Table 2.

With the immunosuppressive protein adsorption material 11 (Comparative Example 2), a generation amount of insoluble microparticles was low, but the LAP-bound TGF-β1 was not able to be efficiently adsorbed.

With the immunosuppressive protein adsorption material 12 (Comparative Example 3), many insoluble microparticles were generated, and the LAP-bound TGF-β1 was also not able to be efficiently adsorbed.

With the immunosuppressive protein adsorption materials 13 to 15 (Comparative Examples 4 to 6), while the LAP-bound TGF-β1 was able to be efficiently adsorbed, many insoluble microparticles were generated.

In Tables below, the following abbreviations are used.
EDA: ethylenediamine
DETA: diethylenetriamine
TEPA: tetraethylenepentamine
PEI600: polyethylenimine with a number average molecular weight of approximately 600
PEI750K: polyethylenimine with a number average molecular weight of approximately 750,000
PAA: polyallylamine with number average molecular weight of approximately 65,000

TABLE 1

| | Example 1 | Example 2 | Example 3 | Example 4 | Example 5 |
|---|---|---|---|---|---|
| | Adsorption Material | | | | |
| | Adsorption Material 1-1 | Adsorption Material 2-1 | Adsorption Material 3 | Adsorption Material 4-1 | Adsorption Material 5 |
| Total Content of Amino Groups (μmol/g) | 51 | 216 | 432 | 578 | 709 |
| Content of Primary Amino Groups (μmol/g) | 9 | 22 | 13 | 30 | 71 |
| Nitrogen-containing Compound | DETA | DETA | DETA | DETA | EDA |
| Amount of Absorption of LAP-bound TGFβ-1 per 1 g of Adsorption Material (ng) | 8.7 | 7.7 | 18.8 | 19.1 | 13.1 |
| Number of Insoluble Microparticles of 25 μm or More (count/mL) | 0.01 | 0.01 | 0.01 | 0.01 | 0.01 |
| Number of Insoluble Microparticles of 10 μm or More (count/mL) | 0.01 | 0.01 | 0.01 | 0.01 | 0.01 |

| | Example 6 | Example 7 | Example 8 | Example 9 | Example 10 |
|---|---|---|---|---|---|
| | Adsorption Material | | | | |
| | Adsorption Material 6 | Adsorption Material 7-1 | Adsorption Material 8-1 | Adsorption Material 9 | Adsorption Material 10 |
| Total Content of Amino Groups (μmol/g) | 785 | 917 | 1601 | 2353 | 2075 |
| Content of Primary Amino Groups (μmol/g) | 87 | 80 | 316 | 432 | 355 |
| Nitrogen-containing Compound | TEPA | DETA | DETA | DETA | TEPA |
| Amount of Absorption of LAP-bound TGFβ-1 per 1 g of Adsorption Material (ng) | 13.5 | 16.2 | 15.9 | 16.4 | 14.3 |
| Number of Insoluble Microparticles of 25 μm or More (count/mL) | 0.01 | 0.01 | 0.01 | 0.01 | 0.01 |
| Number of Insoluble Microparticles of 10 μm or More (count/mL) | 0.01 | 0.01 | 0.01 | 0.01 | 0.01 |

TABLE 2

| | Comparative Example 1 | Comparative Example 2 | Comparative Example 3 | Comparative Example 4 | Comparative Example 5 | Comparative Example 6 |
|---|---|---|---|---|---|---|
| | Adsorption Material | | | | | |
| | Raw Knitted Fabric 1 | Adsorption Material 11 | Adsorption Material 12 | Adsorption Material 13 | Adsorption Material 14 | Adsorption Material 15 |
| Total Content of Amino Groups (μmol/g) | 0 | 2841 | 4887 | 2309 | 2144 | 817 |
| Content of Primary Amino Groups (μmol/g) | 0 | 502 | 938 | 577 | 536 | 603 |
| Nitrogen-containing Compound | None | DETA | DETA | PEI600 | PEI750K | PAA |
| Amount of Absorption of LAP-bound TGFβ-1 per 1 g of Adsorption Material (ng) | 3.2 | 1.8 | 0.3 | 13.1 | 13.8 | 13.6 |

TABLE 2-continued

|  | Comparative Example 1 | Comparative Example 2 | Comparative Example 3 | Comparative Example 4 | Comparative Example 5 | Comparative Example 6 |
|---|---|---|---|---|---|---|
|  |  |  | Adsorption Material |  |  |  |
|  | Raw Knitted Fabric 1 | Adsorption Material 11 | Adsorption Material 12 | Adsorption Material 13 | Adsorption Material 14 | Adsorption Material 15 |
| Number of Insoluble Microparticles of 25 μm or More (count/mL) | 0.01 | 0.01 | 1.53 | 0.32 | 0.35 | 0.44 |
| Number of Insoluble Microparticles of 10 μm or More (count/mL) | 0.01 | 0.01 | 2.34 | 0.63 | 0.66 | 0.75 |

7. Measuring Arithmetic Mean Roughness of Surface

Using a shape measuring laser microscope (made by KEYENCE CORPORATION; Color 3D Laser Scanning Microscope VK-9700), a surface of the adsorption material in a state of being wet with water so as not to be dried was observed at 100-fold magnification, and an arithmetic mean roughness of the surface was measured (compliant with Japanese Industrial Standard B 0601-2001). A reference length L was 50 μm, and a mean value of values measured at ten different positions was the value of the arithmetic mean roughness of the surface.

8. Adhesion Test of Platelet

A batch test using human blood was performed to analyze and calculate adhesiveness of platelets to the adsorption material with a blood cell counting machine. That is, five adsorption materials cut out into disk shapes with diameters of 10 mm were put in a polypropylene container. 3.07 mL of blood drawn from a healthy human was added to this container, and was mixed by inverting for one hour in an incubator at 37° C. After the adsorption material was removed from the container, the number of platelets contained in the residual blood was calculated with the blood cell counter (hereinafter, the number of platelets of blood added with the immunosuppressive protein adsorption material). A similar operation was performed with blood without an addition of the adsorption material (hereinafter, the number of platelets of blood without addition of the immunosuppressive protein adsorption material). The values described above were used to calculate an adhesion rate of platelets by the following Formula 7.

Adhesion rate of platelets (%)=(number of platelets of blood without addition of immunosuppressive protein adsorption material−number of platelets of blood added with immunosuppressive protein adsorption material)/number of platelets of blood without addition of immunosuppressive protein adsorption material×100    Formula 7

EXAMPLE 11

The measurement of arithmetic mean roughness of a surface and the adhesion test of platelets were performed for the immunosuppressive protein adsorption material 4-1. The result is illustrated in Table 3. In the immunosuppressive protein adsorption material 4-1, an adhesion rate of platelets was low.

TABLE 3

| Adsorption Material | Example 11 Adsorption Material 4-1 |
|---|---|
| Nitrogen-containing Compound | DETA |
| Diameter of Fiber (μm) | 20 |

TABLE 3-continued

| Adsorption Material | Example 11 Adsorption Material 4-1 |
|---|---|
| Arithmetic Mean Roughness (μm) | 1.1 |
| Adhesion Rate of Platelets (%) | 45 |

9. Blood Anticoagulant Adsorption Test

Heparin concentrations in a solution before and after an adsorption reaction in the immunosuppressive protein adsorption material were quantitatively determined by a colorimetric assay method using a spectrophotometer, and a heparin adsorption rate by the adsorption material was calculated in accordance with the following Formula 8. That is, four immunosuppressive protein adsorption materials cut out into disk shapes with diameters of 10 mm were put in a polypropylene container having a capacity of 2 mL. A polypropylene container having a capacity of 2 mL without the immunosuppressive protein adsorption material was prepared too. Each of the container with the adsorption material and the container without the adsorption material was added with 1.4 mL of normal saline prepared to have a heparin sodium (AY PHARMACEUTICALS CO., LTD.) concentration of 50 unit/mL, and was mixed by inverting for two hours in an incubator at 37° C. After mixing by inverting, 1 mL of solutions were collected to be respective measurement samples (a sample with adsorption material and a sample without adsorption material). As samples for calibration curve, normal salines prepared to have respective concentrations of 0 unit/mL, 0.3125 unit/mL, 0.625 unit/mL, 1.25 unit/mL, and 2.5 unit/mL were prepared. 50 μL of the respective measurement samples were mixed with 0.95 mL of normal salines to obtain respective measurement samples after dilution. Absorbances at 210 nm were measured with a spectrophotometer for each of the measurement samples and the samples for calibration curve after dilution. Heparin concentrations of the measurement samples after dilution were obtained from the calibration curve, and multiplied by the dilution rate to convert to respective heparin concentrations of the measurement samples before dilution (hereinafter, a heparin concentration of sample with adsorption material and a heparin concentration of sample without adsorption material). The heparin adsorption rate was calculated in accordance with the following Formula 8.

Heparin adsorption rate by adsorption material (%)={(heparin concentration of sample without adsorption material)−(heparin concentration of sample with adsorption material)}/(heparin concentration of sample without adsorption material)×100    Formula 8

EXAMPLES 12 TO 16

Blood anticoagulant adsorption tests were performed for the immunosuppressive protein adsorption materials 1-2, 2-2, 4-2, 7-2, and 8-2. The results are illustrated in Table 4.

With the immunosuppressive protein adsorption materials 1-2, 2-2, 4-2, 7-2, and 8-2 (Examples 12 to 16), the less the total content of amino groups was, the lower the adsorption rate of the heparin was.

TABLE 4

|  | Example 12 Adsorption Material 1-2 | Example 13 Adsorption Material 2-2 | Example 14 Adsorption Material 4-2 | Example 15 Adsorption Material 7-2 | Example 16 Adsorption Material 8-2 |
|---|---|---|---|---|---|
| Total Content of Amino Groups (µmol/g) | 51 | 189 | 540 | 876 | 1716 |
| Content of Primary Amino Groups (µmol/g) | 14 | Not Measured | 33 | Not Measured | Not Measured |
| Nitrogen-containing Compound | DETA | DETA | DETA | DETA | DETA |
| Heparin Adsorption Rate by Adsorption Material (%) | 30.3 | 34.8 | 45.2 | 49.7 | 50.3 |

While contents of primary amino groups are not measured for Examples 13, 15, and 16, all of the contents of primary amino groups in Examples 13, 15, and 16 are estimated to be 450 µmol or less as the adsorption materials 2-2, 7-2, and 8-2 used in these Examples were manufactured by the same process as those of the above-described adsorption materials 2-1, 7-1, and 8-1.

INDUSTRIAL APPLICABILITY

The adsorption material and the adsorption column of the embodiment can efficiently adsorb the immunosuppressive protein. Therefore, an application to cancer therapy is expected. The adsorption material and the adsorption column of the embodiment can be used in combination with the cell infusion treatment that activates the dendritic cells, the natural killer cells, and the like.

REFERENCE SIGNS LIST

1 Container body
2 Inflow port
3 Outflow port
4 Filter
5 Partition plate
5a Opening of partition plate
6 Filter
7 Partition plate
7a Support protrusion of partition plate
7b Through hole of partition plate
8 Pipe
9 Flow passage
10 Through-hole
11 Adsorption material
Q Blood flow

The invention claimed is:

1. An adsorption material for an immunosuppressive protein, the adsorption material comprising:
a water-insoluble carrier to which at least one nitrogen-containing compound is bound,
wherein the nitrogen-containing compound is selected from a polyamine represented by any one of the following Formulas (1-1) to (1-6), and a secondary aliphatic amine represented by the following Formula (3),
wherein a total content of amino groups on the water-insoluble carrier is more than 30 to 2400 µmol per 1 g of the adsorption material,
wherein a proportion of the content of primary amino groups to the total content of amino groups (the content of primary amino groups/the total content of amino groups) is 0.20 or less; and
a content of primary amino groups on the water-insoluble carrier is 450 µmol or less per 1 g of the adsorption material:

$$H_2N-(CH_2)_{p1}-NH_2 \qquad \text{Formula (1-1)}$$

wherein in Formula (1-1), p1 is an integer from 2 to 4, and at least one of the hydrogen atoms of the primary amino groups at both ends is optionally replaced with an alkyl group;

$$H_2N-(CH_2)_{p1}-NH-(CH_2)_{p2}-NH_2 \qquad \text{Formula (1-2)}$$

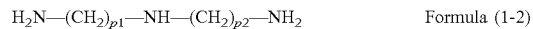

wherein in Formula (1-2), p1 and p2 are each independently an integer from 2 to 5, the hydrogen atom of the secondary amino group is optionally replaced with an alkyl group optionally having an amino group, and at least one of the hydrogen atoms of the primary amino groups at both ends is optionally replaced with an alkyl group;

$$H_2N-(CH_2)_{p1}-NH-(CH_2)_{p2}-NH-(CH_2)_{p3}-NH_2 \qquad \text{Formula (1-3)}$$

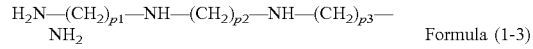

wherein in Formula (1-3), p1, p2, and p3 are each independently an integer from 2 to 5, the hydrogen atoms of the secondary amino groups are optionally each independently replaced with an alkyl group optionally having an amino group, and at least one of the hydrogen atoms of the primary amino groups at both ends is optionally replaced with an alkyl group;

$$H_2N-(CH_2)_{p1}-NH-(CH_2)_{p2}-NH-(CH_2)_{p3}-NH-(CH_2)_{p4}-NH_2 \qquad \text{Formula (1-4)}$$

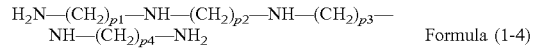

wherein in Formula (1-4), p1, p2, p3, and p4 are each independently an integer from 2 to 5, the sum of p1, p2, p3, and p4 is 17 or less, the hydrogen atoms of the secondary amino groups are optionally each independently replaced with an alkyl group optionally having an amino group, and at least one of the hydrogen atoms of the primary amino groups at both ends is optionally replaced with an alkyl group;

$$H_2N-(CH_2)_{p1}-NH-(CH_2)_{p2}-NH-(CH_2)_{p3}-NH-(CH_2)_{p4}-NH-(CH_2)_{p5}-NH_2 \qquad \text{Formula (1-5)}$$

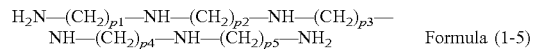

wherein in Formula (1-5), p1, p2, p3, p4, and p5 are each independently an integer from 2 to 5, the sum of p1, p2, p3, p4 and p5 is 16 or less, the hydrogen atoms of the secondary amino groups are optionally each independently replaced with an alkyl group optionally having an amino group, and at least one of the hydrogen atoms of the primary amino groups at both ends is optionally replaced with an alkyl group;

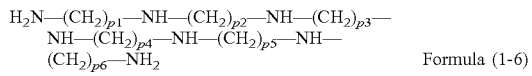

Formula (1-6)

wherein in Formula (1-6), p1, p2, p3, p4, p5, and p6 are each independently an integer from 2 to 5, the sum of p1, p2, p3, p4, p5, and p6 is 15 or less, each of the hydrogen atoms of the secondary amino groups is optionally independently replaced with an alkyl group optionally having an amino group, and at least one of the hydrogen atoms of the primary amino groups at both ends is optionally replaced with an alkyl group;

Formula (3)

wherein in Formula (3), $R^6$ and $R^7$ are each independently a saturated or unsaturated aliphatic hydrocarbon group having 1 to 12 carbon atoms.

2. The adsorption material according to claim 1, wherein the nitrogen-containing compound comprises the polyamine represented by the Formulas (1-1) and (1-2).

3. The adsorption material according to claim 2, wherein the nitrogen-containing compound binds to the water-insoluble carrier via a linker.

4. The adsorption material according to claim 2, wherein the water-insoluble carrier has a form of fiber or particle,
wherein the fiber or the particle has a diameter of 15 to 50 μm, and
wherein the water-insoluble carrier has a surface with an arithmetic mean roughness of 0.1 to 3.0 μm.

5. A method of capturing an immunosuppressive protein, wherein said method comprises immersing the adsorption material according to claim 2 into a container having a solution with said immunosuppressive protein, thereby capturing the immunosuppressive protein by binding the immunosuppressive protein to the adsorption material,
wherein the immunosuppressive protein is a TGF-β or a LAP-bound TGF-β.

6. A method of capturing an immunosuppressive protein, wherein said method comprises immersing the adsorption material according to claim 1 into a container having a solution with said immunosuppressive protein, thereby capturing the immunosuppressive protein by binding the immunosuppressive protein to the adsorption material,
wherein the immunosuppressive protein is a TGF-β or a LAP-bound TGF-β.

7. The method of capturing an immunosuppressive protein according to claim 6,
wherein the immunosuppressive protein is the LAP-bound TGF-β.

8. The adsorption material according to claim 1,
wherein the nitrogen-containing compound binds to the water-insoluble carrier via a linker.

9. The adsorption material according to claim 8,
wherein the water-insoluble carrier has a form of fiber or particle,
wherein the fiber or the particle has a diameter of 15 to 50 μm, and
wherein the water-insoluble carrier has a surface with an arithmetic mean roughness of 0.1 to 3.0 μm.

10. A method of capturing an immunosuppressive protein, wherein said method comprises immersing the adsorption material according to claim 3 into a container having a solution with said immunosuppressive protein, thereby capturing the immunosuppressive protein by binding the immunosuppressive protein to the adsorption material,
wherein the immunosuppressive protein is a TGF-β or a LAP-bound TGF-β.

11. The adsorption material according to claim 1,
wherein the water-insoluble carrier has a form of fiber or particle,
wherein the fiber or the particle has a diameter of 15 to 50 μm, and
wherein the water-insoluble carrier has a surface with an arithmetic mean roughness of 0.1 to 3.0 μm.

12. The method of capturing an immunosuppressive protein according to claim 6,
wherein the immunosuppressive protein is the TGF-β.

13. An adsorption column comprising the adsorption material according to claim 1.

14. A method of purifying blood, wherein said method comprises immersing the adsorption column according to claim 8 in a container with saline solution and said blood,
wherein microparticles from said blood are captured by the adsorption column and said microparticles are 10 μm or more in size.

* * * * *